(12) United States Patent
Shi et al.

(10) Patent No.: US 6,231,857 B1
(45) Date of Patent: May 15, 2001

(54) **ANTIBODIES TO *S. MUTANS* AND USES THEREOF**

(75) Inventors: Wenyuan Shi; Wyatt R. Hume, both of Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/378,247

(22) Filed: Aug. 20, 1999

Related U.S. Application Data

(60) Provisional application No. 60/102,179, filed on Sep. 28, 1998.

(51) Int. Cl.$^7$ .................................................. A61K 39/40
(52) U.S. Cl. .................................. 424/165.1; 424/130.1; 424/141.1; 530/388.1; 530/388.4; 530/388.2; 435/243; 435/325; 435/326; 435/332; 435/354
(58) Field of Search ........................... 530/350, 387.1, 530/388.1, 388.4, 388.2; 435/243, 325, 326, 332, 354; 424/244.1, 130.1, 141.1, 165.1

(56) References Cited

U.S. PATENT DOCUMENTS

| | | |
|---|---|---|
| 4,150,116 | 4/1979 | Taubman et al. ........................ 424/94 |
| 4,250,262 | 2/1981 | Taubman et al. ..................... 435/193 |
| 4,324,782 | 4/1982 | Beck ....................................... 424/87 |
| 4,442,085 | 4/1984 | Colman et al. .......................... 424/49 |
| 4,448,768 | 5/1984 | Colman et al. .......................... 424/92 |
| 4,521,513 | 6/1985 | Russell .................................. 435/68 |
| 4,693,888 | 9/1987 | Miyahara et al. ....................... 424/49 |
| 4,725,428 | 2/1988 | Miyahara et al. ....................... 424/50 |
| 5,281,524 | 1/1994 | Horikoshi et al. .................... 435/193 |
| 5,352,446 | 10/1994 | Lehner ............................... 424/150.1 |
| 5,352,450 | 10/1994 | Koga et al. .......................... 424/190.1 |
| 5,439,680 | 8/1995 | Horikoshi et al. ................. 424/157.1 |
| 5,518,721 | 5/1996 | Lehner et al. ...................... 424/150.1 |
| 5,612,031 | 3/1997 | Lehner et al. ...................... 424/150.1 |
| 5,686,075 | 11/1997 | Taubman et al. ................. 424/197.11 |
| 5,875,798 | 3/1999 | Petrus .................................. 132/321 |

OTHER PUBLICATIONS

Shi, Jewett, and Hume; Rapid and Quantitative Detection of *Streptococcus Mutans* with Species–Specific Monoclonal Antibodies; Aug. 8, 1998; pp. 365–371.
Soet, van Dalen, and de Graaff; Identification of Mutans Streptococci with Monoclonal Antibodies; 1990; pp. 219–225.
De Soet, Holbrook, Magnusdottir, and De Graaff; *Streptococcus Sobrinus* and *Streptococcus Mutans* in a Longitudinal Study of Dental Caries; 1993; pp. 237–243.
Akiyama; Monoclonal Antibodies Specific for a Polysaccharide Antigenic Determinant of *Streptococcus Mutans*; 1995; pp. 360–372.
Database WPI; Monoclonal Antibody Specific *Streptococcus Mutans* Preparation Isolate Antibody Produce Cell Mouse Immune Mouse Myeloma Cell; Derwent Publications Ltd; Jul. 10, 1990; Week 9033.
Database WPI; Monoclonal Antibody Specific *Streptococcus Mutans* Preparation Isolate Antibody Produce Cell Mouse Immune Antigen Fuse Mouse Myeloma Cell; Derwent Publications Ltd; Jul. 10, 1990; Week 9033.
Database WPI; Monoclonal Antibody Oral Composition B ase Diagnose Investigate Respond *Streptococcus Mutans* Prevent Caries; Derwent Publications Ltd; Jul. 10, 1990; Week 9816.
Gazi; Monoclonal Antibodies in Dentistry; British Dental Journal; Dec. 6, 1986; vol. 161, No. 11; pp. 399–405.
Van Raamsdonk, de Soet, Bosch–Tijhof; and de Graaff; Oral Microbiology and Immunology; Effect of Antibodies on Chemiluminescencce and on Killing of *Streptococcus Sobrinus* by Polymorphonuclear Leukocytes; vol. 11, No. 4, Aug. 1996; pp. 254–258.
Van Raamsdonk, de Soet, and de Graaff; Caries Research; Effect of Monoclonal Antibodies on the Colonization of rats by *Streptococcus Sobrinus*; Jan. 27, 1993; pp. 27: 31–37.
Lehner, Ma, and Kelly; Genetically Engineered Vaccines; Advances in Experimental Medicine and Biology; vol. 327; A Mechanism of Passive Immunization with Monoclonal Antibodies to a 185,000M$_r$ Streptococcal Antigen; 1992; pp. 151–163.
Ma, Hikmat, Wycoff, Vine, Chargelegue, Yu, Hein, and Lehner; Nature Medicine; vol. 4, No. 5; May 1998; Characterization of a Recombinant Plant Monoclonal Secretory Antibody and Preventive Immunotherapy in Humans; p. 601–606.
Ma, Smith, and Lehner; Use of Monoclonal Antibodies in Local Passive Immunization to Prevent Colonization of Human Teeth by *Streptococcus Mutans*; Infection and Immunity, May 1987, vol. 55, No. 5; pp. 1274–1278.
Everhart, Mallett and Doyle; Microbiological Sciences, Dental Caries Vaccine: Some Problems Solved; vol. 2, No. 10; 1985; pp. 312–313.
Ma, Hunjan, Smith, Kelly, and Lehner; Infection and Immunity; An Investigation into the Mechanism of Protection by Local Passive Immunization with Monoclonal Antibodies Against *Streptococcus Mutans*; Oct. 1990; vol. 58, No. 10; pp. 3407–3414.

(List continued on next page.)

*Primary Examiner*—Jennifer Graser
(74) *Attorney, Agent, or Firm*—Oppenheimer, Wolff & Donnelly LLP

(57) ABSTRACT

The invention describes three monoclonal IgG antibodies, referred to as SWLA1, SWLA2, and SWLA3, which appear to recognize a species-specific lipooligosaccharide or lipopolysaccharide on the cell surface of *S. mutans*. The invention also describes a rapid method of detection of *S. mutans* without the need for prior growth of the bacteria in culture. The invention further describes a methods of utilizing these antibodies for rapidly quantitatively detecting *S. mutans*. These methods are sensitive enough to detect the presence of a single *S. mutans* bacterial cell. These methods can be widely used in the clinical diagnosis and treatment of dental caries in humans.

6 Claims, 2 Drawing Sheets

OTHER PUBLICATIONS

Kobayashi, Izumi, Okamura, Matsui, Ishibashi, and Sakai; Caries Research; Biological Behavior of Human Dental Pulp Cells in Response to *Carious Stimuli* Analyzed by PCNA Immunostaining and AgNOR Staining; May–Jun. 1996; pp. 225–230.

Arakawa and Langridge; Nature Medicine; Plants are not Just Passive Creatures; vol. 4, No. 5, May 1998, pp. 550–551.

Lehner, Caldwell, and Smith; Infection and Immunity; Local Passive Immunization by Monoclonal Antibodies Against Streptococcal Antigen I/II in the Prevention of Dental Caries; Dec. 1985, vol. 50, No. 3, pp. 796–799.

Shi, Jewett, and Hume; Hybridoma; Rapid and Quantitative Detection of *Streptococcus Mutans* with Species–Specific Monoclonal Antibodies; vol. 17, No. 4, 1998; pp. 365–371.

ANTIBODIES TO S. MUTANS AND USES THEREOF

CROSS-REFERENCES

This application claims priority from a U.S. provisional application, U.S. application Ser. No. 60/102,179, filed Sep. 28, 1998.

BACKGROUND OF THE INVENTION

The present invention relates to novel antibodies to the *Streptococcus mutans* bacteria that are naturally found in the mouth, and play a role in the development of dental caries. The invention relates to methods of detection of *S. mutans* using the antibodies of the invention or fragments or derivatives thereof. The invention also relates to diagnosing, monitoring, treating and protecting the teeth from dental caries using the antibodies of the invention or fragments or derivatives thereof.

Throughout this application, various publications are referenced within parentheses and cited at the end of the application. The disclosures of these publications are hereby incorporated by reference herein in their entireties.

Currently human dental caries, or cavities, are detected by changes in translucency, color, hardness or X-ray density of teeth. These technologies have limitations both in specificity and reproducibility. Further, they do not show, at a single time point, whether or not the disease is active.

The bacterium *Streptococcus mutans*, or *S. mutans* (named and described by Clark in 1924) is known to be a prime etiologic agent for the initiation and progression of human dental caries. (Fitzgerald and Keyes, 1960; Loesche, 1982; Loesche, 1986; Tanzer, 1997). *S. mutans* is one of the primary factors in acid dissolution of the apatite (mineral) component of the enamel then the dentin, or of the cementum then the dentin. A strong correlation between the proportion of *S. mutans* in dental plaque or in saliva relative to other bacterial species and the presence or risk of future outbreaks of dental caries has been documented, (Tanzer, 1997; Krasse, 1988). Therefore, *S. mutans* in plaque or saliva can serve as an index for both caries activity state and caries risk or susceptibility (Loesche et al., 1975; Ellen, 1976; Krasse, 1985; Krasse, 1988). These indices play an increasingly important role in the diagnosis and treatment of dental caries (Hume, 1993; Mundorff et al., 1993; Van Houte, 1993).

Present techniques of detection and quantitative determination of *S. mutans* include bacterial culture with selective media using either broth or agar plate systems (Ellen, 1976; Loesche, 1982) and polymerase chain reaction techniques (Igarashi et al., 1996). Each of these methods requires significant time (on the order of days), well trained personnel and sophisticated equipment to perform. Consequently, existing techniques are relatively expensive and time consuming.

Alternatively, monoclonal antibody based detection methods allow a rapid and accurate, yet economic quantitative measurement of the presence of bacterial cells, and have significant advantages compared to traditional culture sensitivity assays or polymerase chain reaction (PCR) techniques. Bacteria produce unique polysaccharide structures of lipooligosaccharide or lipopolysaccharide or other polysaccharides, among a large range of other chemical components and products, on their cell surfaces. Monoclonal antibodies can be raised against these chemical structures, using standard hybridoma techniques (Kohler and Milstein, 1975). The sensitivity and accuracy of this method is largely dependent on the specificity of the monoclonal antibody produced. By making and screening large numbers of hybrid cell lines, one can find certain monoclonal antibodies which are species-specific for the desired bacteria, i.e. the monoclonal antibodies ICL 11 and ICL12 recognize the 0139 antigen of *Vibrio cholerae* (Hasan, 1994)). These monoclonal antibodies can be linked to various detection systems including, for example, fluorescent reagents, calorimetric reagents or coagglutination reagents. The resulting labeled antibodies can specifically bind to the desired bacterium in any sample, and rapidly present the result through the linked detection systems (Harlow and Lane, 1988).

TABLE 1

|  | PCR | Culture Sensitivity | monoclonal antibody |
|---|---|---|---|
| Reporting time | 2 days send out samples | 7–10 days send out samples | 3–10 min instant results at chairside |
| Cost | ~$100 | ~$100 | less than $10 |
| Precision | Species level | genus level | Species level |
| Test sensitivity | few hundred cells regardless of viability | only cultivable cells need viable cells | few hundred cells regardless of viability |
| Accuracy | >90% | ~50% | >90% |
| Lab requirement | yes | yes | no |

Due to overwhelming advantages, monoclonal antibody-based detection methods have been widely used in medical microbiology. At present, there are nearly one hundred different monoclonal antibody based detection methods available to diagnose various pathogenic bacteria. However, to date there have been no such methods available for the detection of dental caries. While other investigators have made monoclonal antibodies to *S. mutans*, these monoclonal antibodies are not suited for diagnostic or clinical uses because they are not species specific for *S. mutans* and cannot detect the presence of *S. mutans* at very low levels. Almost all previous monoclonal antibodies were made against surface proteins of *S. mutans* (i.e. glucosyltransferase, agglutinin, surface antigen PI, etc.). Similar proteins can also be found on other Streptoccocci species. Thus, these monoclonal antibodies can not be used to distinguish *S. mutans* from other Streptoccocci species. To diagnose dental caries it is important to be able to discern the *S. mutans* strain from other bacteria that may be present. One needs to find a monoclonal antibody that is specific for a unique epitope specific to the *S. mutans* cell surface.

SUMMARY OF THE INVENTION

Accordingly, the invention describes three monoclonal IgG antibodies, referred to as SWLA1, SWLA2, and SWLA3, which appear to recognize a species-specific polysaccharide on the cell surface of *S. mutans*. The invention also describes a rapid method of detection of *S. mutans* without the need for prior growth of bacteria in culture. The invention further describes methods of utilizing these antibodies for rapidly quantitatively detecting *S. mutans*. These methods are sensitive enough to detect the presence of a single *S. mutans* bacteria cell. These methods can be widely used in the clinical diagnosis and treatment of dental caries. Yet another embodiment of the invention is a diagnostic kit containing the monoclonal antibodies of the invention and reagents for detecting binding of the antibodies to *S. mutans* cells on teeth in or in a sample from a subject.

In particular, one aspect of the present invention is a monoclonal antibody that specifically binds an antigen on the surface of Streptococcus mutans and which is the monoclonal antibody produced by a hybridoma deposited with the American Type Culture Collection as ATCC No. HB12559, and which is designated SWLA1.

Another aspect of the present invention is a monoclonal antibody that specifically binds an antigen on the surface of S. mutans and which is the monoclonal antibody produced by a hybridoma deposited with the American Type Culture Collection as ATCC No. HB 12560, and which is designated SWLA2.

Yet another aspect of the present invention is a monoclonal antibody that specifically binds an antigen on the surface of S. mutans and which is the monoclonal antibody produced by a hybridoma deposited with the American Type Culture Collection as ATCC No. HB 12258, and which is designated SWLA3.

BRIEF DESCRIPTION OF THE DRAWINGS

The following invention will become better understood with reference to the specification, appended claims, and accompanying drawings, where:

DETAILED DESCRIPTION OF THE INVENTION

Figure 1A:
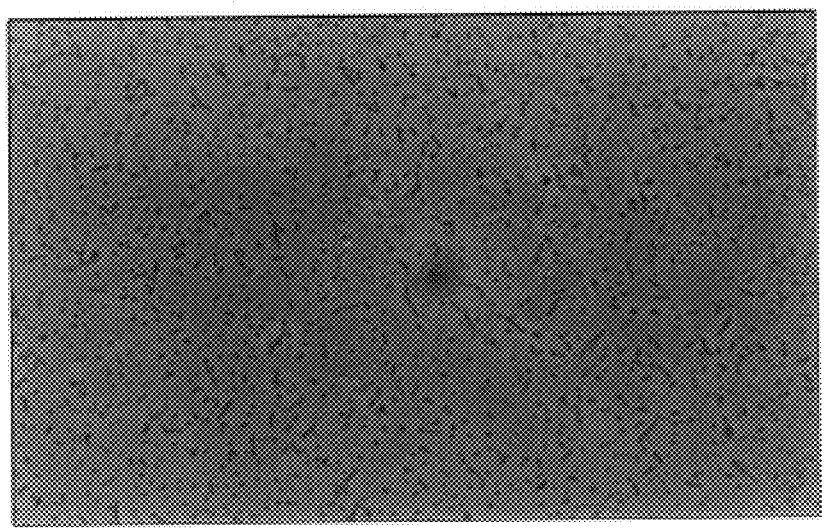
FIG. 1 shows the detection of S. mutans SWLA1 with fluorescence microscopy; the S. mutans cells (ATCC25175) were labeled as described in Example 1, infra; 1(a) shows a regular phase-contrast light microscope image of a bacteria mixture containing S. rattus, S. gordonii, S. mitis, S. sanguis, E. coli, and S. mutans with FITC conjugated monoclonal antibodies; 1(b) shows the same group of bacteria under fluorescent lighting; the bright spots are all S. mutans, indicating that the SWLAI monoclonal antibody specifically recognizes S. mutans.

The invention describes three species-specific monoclonal IgG antibodies, referred to as SWLA1, SWLA2, and SWLA3, which recognize a species-specific epitope on the cell surface of S. mutans, and conjugates thereof, which appears to be a species-specific polysaccharide. The invention includes methods of using the monoclonal antibodies to detect quantity and presence of S. mutans to monitor the onset and severity of dental caries.

The monoclonal antibodies SWLA1, SWLA2, and SWLA3 can be prepared by hybridoma fusion techniques or by techniques that utilize EBV-immortalization technologies. Hybridoma fusion techniques were first introduced by Kohler and Milstein (see, Kohler and Milstein, (1975); Brown et al., (1981); Brown et al., (1980); Yeh et al., (1976); and Yeh et al., (1982)).

These techniques involve the injection of an immunogen (e.g., purified antigen or cells or cellular extracts carrying the antigen) into an animal (e.g., a mouse) so as to elicit a desired immune response (i.e., production of antibodies) in that animal. For example, S. mutans may be used as the immunogen. In the illustrative example herein, S. Mutans strain ATCC25175 was used as the immunogen. The cells are injected repeatedly, for example, into a mouse and, after a sufficient time, the mouse is sacrificed and somatic antibody-producing cells are obtained. The use of other mammalian models, for example rat, rabbit and frog somatic cells, is also possible. The cell chromosomes encoding desired immunoglobulins are immortalized by fusing them with myeloma cells, generally in the presence of a fusing agent such as polyethylene glycol (PEG). Any of a number of myeloma cell lines may be used as a fusion partner according to standard techniques; for example, the P3-NSI/1-Ag4-1, P3-x63-Ag8.653 or Sp2/0-Ag14 myeloma lines. These myeloma lines are available from the American Type Culture Collection (ATCC), in Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (Zola et al. (1982)). Hybridomas produced according to these methods can be propagated in vitro or in vivo (in ascites fluid) using techniques known in the art (see, generally, Fink et al., supra, 1984).

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

For certain therapeutic applications chimeric (mouse-human) or human monoclonal antibodies may be preferable to murine antibodies, because patients treated with mouse antibodies generate human antimouse antibodies. (Shawler et al., (1985)). Chimeric mouse-human monoclonal antibodies reactive with S. mutans can be produced, for example, by techniques developed for the production of chimeric antibodies (Oi et al., (1986); Liu et al., (1987)). Accordingly, genes coding for the constant regions of the SWLAI, SWLA2, or SWLA3 antibody molecule are substituted with human genes coding for the constant regions of an antibody with appropriate biological activity (such as the ability to selectively bind *S. mutans*).

Novel antibodies of mouse or human origin can be also made that are analogous to the SWLA1, SWLA2, or SWLA3 antibody and that have the appropriate biological functions. These antibodies can have complementarity-determining regions (CDRs) that are identical to one of SWLA1, SWLA2, or SWLA3. Alternatively, these antibodies can bind an antigen on the surface of *S. mutans* and can compete at least about 80% as effectively on a molar basis with at least one of SWLA1, SWLA2, or SWLA3 as SWLA1, SWLA2, or SWLA3 for binding to the antigen on the surface of *S. mutans*. These antibodies have substantially no reactivity with any of the following bacterial strains: *Streptococcus rattus* ATCC19645, *Streptococcus gordonii* ATCC10558, *Streptococcus gordonii* ATCC13396, *Streptococcus mitis* ATCC49456, *Streptococcus sobrinus* ATCC33478, *Streptococcus sobrinus* 6715, *Streptococcus sanguis* ATCC10556, *Streptococcus sanguis* ATCC49295, *Streptococcus anginosus* ATCC33397, *Lactobacillus acidophilus* ATCC4356, *Lactobacillus casei* ATCC4646, *Actinobacillus actinomycetemcomitans* ATCC 33384, *Porphyromonas gingivalis* ATCC33277, *Prevotella intermedia* ATCC49046, *Bacteroides forsythus* ATCC43047, *Eikenella corrodens* ATCC23834, *Fusobacterium nucleatum* ATCC25586, *Treponema denticola* ATCC33520, *Campylobacter rectus* ATCC33238, *Myxococcus xanthus* DZ2, and *Escherichia coli* HB101. Preferably, the monoclonal antibody competes at least about 90% as effectively on a molar basis.

For example, human monoclonal antibodies may be made by using the antigen, e.g. the portion of the polysaccharide on the cell surface of *S. mutans*, which binds the antibodies SWLA1, SWLA2, or SWLA3 of the invention, to sensitize human cells to the antigen in vitro followed by EBV-transformation or hybridization of the antigen-sensitized cells with mouse or human cells, as described by Borrebaeck et al. (1988).

The antibodies of this invention were produced via hybridoma techniques. NSL/Ag4.1 mouse myeloma cell line was used as a fusion partner, and whole cells of type c *S. muians* strain ATCC25175 were used as the immunogen as described in the Example, infra. The hybridomas produced were screened. When this was performed three species-specific monoclonal antibodies against *S. mutans* were obtained designated SWLA1, SWLA2, and SWLA3. The hybridomas, producing the SWLA1, SWLA2, and SWLA3 antibodies, have been deposited with the American Type Culture Collection, 10801 University Boulevard, Manassas, Va. 20110-2209, on Aug. 25, 1998 under the provisions of the Budapest Treaty, and are identified as follows:

SWLA1 Accession No.: HB-12559
SWLA2 Accession No.: HB-12560
SWLA3 Accession No.: HB-12558

The three monoclonal antibodies were found to be of the IgG subtype. Western blot and other biochemical analysis shows that they are against unique polysaccharide on cell surface of *S. mutans*. Western blot techniques are well known by one skilled in the art (Golub, E. S. and D. R. Green, 1991).

These monoclonal antibodies are very different from the monoclonal antibodies found in the prior art. Those antibodies were made against surface proteins that are found on many other bacteria and not the species-specific polysaccharide, which the instant antibodies recognize. This difference makes the prior antibodies acceptable for research purposes but not diagnostic purposes (Carien and Olsson, 1995; Chia et al., 1993; Fukushima et al., 1993; Brady, et al., 1991). Due to the specificity for *S. mutans*, the monoclonal antibodies of this invention are particularly useful for diagnosis and treatment of human dental caries. Because the monoclonal antibody of the invention are able to detect low numbers of *S. mutans* cells in small samples they are able to be used to screening for *S. mutans* cells. These monoclonal antibodies also permit the development of simple and inexpensive dental caries detection methods that could be used for caries risk assessment at a dentist's chairside or in the patient's household.

The most preferred antibodies will selectively bind to *S. mutans* and will not bind (or will bind weakly) to non- *S. mutans* bacteria. The antibodies that are particularly contemplated include monoclonal antibodies as well as fragments of monoclonal antibodies containing an *S. mutans* antigen-binding domain. The invention also encompasses antibody fragments that specifically recognize *S. mutans*. As used herein, an antibody fragment is defined as at least a portion of the immunoglobulin molecule which binds to its target, i.e., the antigen binding region on the *S. mutans*. This includes Fv, Fab, Fab' and F(ab)'$_2$ fragments of appropriate specificity.

The invention fiirther includes a human monoclonal antibody that specifically binds an antigen found on the surface of *S. mutans*. The antigen that is bound is one of those bound by at least one of the monoclonal antibody produced by a hybridoma deposited with the American Type Culture Collection as ATCC No. HB 12559 and designated SWLA1, the monoclonal antibody produced by a hybridoma deposited with the American Type Culture Collection as ATCC No. HB 12560 and designated SWLA2, and the monoclonal antibody produced by a hybridoma deposited with the American Type Culture Collection as ATCC No. HB 12558 and designated SWLA3. The human monoclonal antibody has substantially no reactivity with any of the following bacterial strains: *Streptococcus rattus* ATCC19645, *Streptococcus gordonii* ATCC10558, *Streptococcus gordonii* ATCC13396, *Streptococcus mitis* ATCC49456, *Streptococcus sobrinus* ATCC33478, *Streptococcus sobrinus* 6715, *Streptococcus sanguis* ATCC10556, *Streptococcus sanguis* ATCC49295, *Streptococcus anginosus* ATCC33397, *Lactobacillus acidophilus* ATCC4356, *Lactobacillus casei* ATCC4646, *Actinobacillus actinomycetemcomitans* ATCC 33384, *Porphyromonas gingivalis* ATCC33277, *Prevotella intermedia* ATCC49046, *Bacteroides forsythus* ATCC43047, *Eikenella corrodens* ATCC23834, *Fusobacterium nucleatum* ATCC25586, *Treponema denticola* ATCC33520, *Campylobacter rectus* ATCC33238, *Myxococcus xanthus* DZ2, and *Escherichia coli* HB101.

Methods for the preparation of human monoclonal antibodies are known in the art and include phage display techniques and isolation of human hybridomas using B lymphocytes from patients producing antibodies against *S. mutans*, as well as in vitro immunization techniques. Such techniques are well known in the art and are described, for example, in C. A. K. Borrebaeck, ed., "Antibody Engineering" (2d ed., Oxford University Press, New York, 1995), incorporated herein by this reference.

The invention further includes chimeric antibodies, including humanized antibodies. This includes chimeric antibodies that have complementarity-determining regions that are identical with the complementarity-determining regions of one of:
(a) a monoclonal antibody produced by a hybridoma deposited with the American Type Culture Collection as ATCC No. HB 12559 and designated SWLA1;
(b) a monoclonal antibody produced by a hybridoma deposited with the American Type Culture Collection as ATCC No. HB 12560 and designated SWLA2; or
(c) a monoclonal antibody produced by a hybridoma deposited with the American Type Culture Collection as ATCC No. HB 12558 and designated SWLA3.

Also within the scope of the invention are chimeric antibodies that have complementarity-determining regions that are identical with the complementarity-determining regions of an antibody that binds an antigen on the surface of *S. mutans* and can compete at least about 80% as effectively on a molar basis with at least one of SWLA1, SWLA2, or SWLA3 as SWLA1, SWLA2, or SWLA3 for binding to the antigen on the surface of *S. mutans*. These chimeric antibodies, as described above, have substantially no reactivity with any of the following bacterial strains: *Streptococcus rattus* ATCC19645, *Streptococcus gordonii* ATCC10558, *Streptococcus gordonii* ATCC13396, *Streptococcus mitis* ATCC49456, *Streptococcus sobrinus* ATCC33478, *Streptococcus sobrinus* 6715, *Streptococcus sanguis* ATCC10556, *Streptococcus sanguis* ATCC49295, *Streptococcus anginosus* ATCC33397, *Lactobacillus acidophilus* ATCC4356, *Lactobacillus casei* ATCC4646, *Actinobacillus actinomycetemcomitans* ATCC 33384, *Porphyromonas gingivalis* ATCC33277, *Prevotella intermedia* ATCC49046, *Bacteroides forsythus* ATCC43047, *Eikenella corrodens* ATCC23834, *Fusobacterium nucleatum* ATCC25586, *Treponema denticola* ATCC33520, *Campylobacter rectus* ATCC33238, *Myxococcus xanthus* DZ2, and *Escherichia coli* HB101.

These chimeric antibodies specifically bind an antigen on the surface of *S. mutans* and which have at least a portion of the amino acid sequence of the heavy chain or the light chain of a different species origin than the species origin of the complementarity-determining regions. In one alternative, at least a portion of the amino acid sequence of the heavy chain or the light chain is of human origin so that the chimeric antibody is a humanized antibody. In a version of this alternative, substantially all of the amino acid sequences of the heavy chain and the light chain outside the complementarity-determining regions are of human origin.

As indicated, chimeric antibodies according to the present invention may have a non-human antigen-binding site and a humanized effector binding region. The non-human antigen-binding portion may include, but is not limited to, a murine, canine, feline or other veterinary model or other mammalian antigen-binding site.

Methods for producing chimeric antibodies, including humanized antibodies, are well known in the art and are described, for example, in C. A. K. Borrebaeck, ed., "Antibody Engineering" (2d ed., Oxford University Press, New York, 1995), incorporated herein by this reference.

The invention further includes single-chain binding fragments, known generally as sFv, that have the appropriate specificity for the antigen on the cell surface of *S. mutans* as defined above. Methods for preparing such sFv are generally known in the art and are described, for example, in C. A. K. Borrebaeck, ed., "Antibody Engineering" (2d ed., Oxford University Press, New York, 1995), incorporated herein by this reference.

The specificity of the SWLA1, SWLA2, and SWLA3 antibodies for *S. mutans* antigen make these antibodies excellent markers for screening, diagnosis, prognosis, and follow-up assays, imaging methodologies, and therapeutic methods in the management of dental caries. The invention provides various immunological assays useful for the detection of *S. mutans* and for the diagnosis of dental caries or the risk thereof. This includes various immunological assay formats well known in the art, including, but not limited to, various types of radioimmunoassays, enzyme-linked immunosorbent assays (ELISA), enzymelinked immunofluorescent assays (ELIFA), and the like. In addition, immunological imaging methods capable of detecting dental caries are also provided by the invention, including but not limited to a colloidal-gold based colorimetric assay, and radioscintigraphic imaging methods using radiolabeled SWLA1, SWLA2, and SWLA3 antibodies (e.g., U.S. Pat. No. 4,920,059 issued Apr. 24, 1990; U.S. Pat. No. 5,079,172 issued Jan. 7, 1992). In addition the antibodies of the invention can be conjugated with other dyes or fluorescent markers and used directly on the tooth to image caries. Such assays may be clinically useful in the detection and monitoring of dental caries. Such assays generally comprise using one or more of the SWLA1, SWLA2, and SWLA3 antibodies.

In addition to the immunological assays and imaging methods, the invention also includes an immunoconjugate comprising a molecule containing the antigen-binding region of the SWLA1, SWLA2, or SWLA3 antibody, or a fragment thereof containing the antigen binding region, joined to for example a therapeutic agent, a diagnostic agent or a cytotoxic agent for treatment of dental caries. Examples of cytotoxic agents include, but are not limited to, chlorhexidine, fluoride, ricin, doxorubicin, daunorubicin, taxol, ethidium bromide, mitomycin, etoposide, tenoposide, vincristine, vinblastine, colchicine, dihydroxyanthracenedione, actinomycin D, diphtheria toxin, *Pseudomonas exotoxin* (PE) A, PE40, abrin, glucocorticoid and radioisotopes.

The SWLA1, SWLA2, and SWLA3 monoclonal antibodies of the invention are useful for diagnostic applications, both in vitro and in vivo, for the detection of dental caries. In vitro diagnostic methods are well known in the art (see, e.g., Roth, supra 1986, and Kupchik, supra 1988), and include immunohistological detection of dental caries or serologic detection of *S. mutans* (e.g., in saliva samples or other biological fluids).

Immunohistological techniques involve contacting a biological specimen, such as a saliva, tartar, or plaque specimen, with the antibody of the invention and then detecting the presence in the specimen of the antibody complexed to its antigen. The formation of such antibody-antigen complexes with the specimen indicates the presence of the antigen, *S. mutans*. Detection of the antibody in the specimen can be accomplished using techniques known in the art, such as the immunoperoxidase staining technique, the avidin-biotin (ABC) technique or immunofluorescence techniques (Ciocca et al., (1986); Helistrom et al., (1986); and Kimball (ed.,), (1986)).

Serologic diagnostic techniques involve the detection and quantitation of *S. mutans* antigens that have been secreted or "shed" into the saliva or other biological fluids of patients with dental caries. Such antigens can be detected in the saliva using techniques known in the art such as radioimmunoassays (RIA) or enzyme-linked immunosorbent assays (ELISA) wherein an antibody reactive with the "shed" antigen is used to detect the presence of the antigen in a fluid sample (see, e.g., Uotila et al., (1981) and Allum et al., 1986). These assays, using the antibodies disclosed herein, can therefore be used for the detection of *S. mutans* in biological fluids. Thus, it is apparent from the foregoing that the antibodies of the invention can be used in most assays involving antigen-antibody reactions. These assays include, but are not limited to, standard RIA techniques, both liquid and solid phase, as well as ELISA assays, immunofluorescence techniques, and other immunocytochemical assays (see, e.g., Sikora et al. (1984)).

The antibodies of the invention are also useful for in vivo diagnostic applications for the detection of dental caries. One such approach involves the detection of dental caries in vivo by imaging techniques using the antibody labeled with an appropriate imaging reagent that produces a detectable signal when bound to *S. mutans*. Imaging reagents and procedures for labeling antibodies with such reagents are well known (see, e.g., Wensel and Meares, (1983); Colcher et al., (1986)). The labeled antibody may be detected by a technique such as radionuclear scanning (see, e.g., Bradwell et al. (1985)).

The antibody fragments used in the immunoconjugates can include Fv, Fab, Fab' or F(ab)'$_2$ fragments. Use of immunologically reactive fragments, such as the Fv, Fab, Fab', or F(ab)'$_2$ fragments, is often preferable, especially in a therapeutic context, as these fragments are generally less immununogenic than the whole immunoglobulin. These antibodies, as well as unconjugated antibodies, may be useful therapeutic agents naturally targeted to *S. mutans* cells to kill the cells, thus preventing and or treating dental caries resulting from the accumulation of *S. mutans*. Techniques for conjugating therapeutic agents to antibodies are well known (see, e.g., Arnon et al., 1985; Hellstrom et al. 1987; Thorpe, (1985); and Thorpe et al., (1982)).

The SWLA1, SWLA2, and SWLA3 antibodies may also be used in methods for purifing *S. mutans* proteins and peptides and for isolating homologues and related molecules. Methods for purification of proteins and peptides using antibodies as capture reagents are well known in the art. For example, in one embodiment, a method of purifying an *S. mutans* protein comprises incubating a SWLA1, SWLA2, or SWLA3 antibody, which has been coupled to a solid matrix, with a lysate or other solution containing *S. mutans* proteins or peptides, under conditions which permit the SWLA1, SWLA2, or SWLA3 antibody to bind to the *S. mutans* protein or peptides; washing the solid matrix to eliminate impurities; and eluting the *S. mutans* proteins or fragments from the coupled antibody.

The invention further includes a method for detecting the presence of *S. mutans* on teeth in a subject or in a saliva, plaque, or tartar sample from a subject, comprising contacting at least one tooth or the sample with the SWLA1, SWLA2, or SWLA3 antibody and detecting the binding of the antibody with the *S. mutans* on the tooth and or in the sample. The antibody can be administered by topical application to the surface of the teeth by means including in a toothpaste, mouthwash, lozenge, gel, powder, spray, liquid, tablet, or chewing gum. One can detect the presence of *S. mutans* by determining the presence of a complex formed between the monoclonal antibodies and *S. mutans* cells as a result of contacting the tooth and or the sample with a labeled antibody, the complex being indicative of the presence of *S. mutans* in the sample. The antibodies of the invention can be labeled so as to directly or indirectly produce a detectable signal. The label can for example be selected from the following compounds a radiolabel, an enzyme, a chromophore, a chemiluminescent moiety, a bioluminescent moiety, or a fluorescer. When a fluorescer is used the fluorescence can be detected by means of fluorescence microscopy, fluorometer, or by flow cytometry. A colloidal gold colorimetric system can also be used to detect the presence of *S. mutans*. The colloidal gold system is Well known in the art. (J. A. K. Hasan, et al. (1994); and E. Harlow, D. Lane. (1988)).

The invention also includes a method for diagnosing, in a subject, the early onset of dental caries. This can be accomplished by quantitatively determining on at least one tooth in a subject, or in a saliva, plaque, or tartar sample from a subject, the number of *S. mutans* present using an antibody of the invention and comparing the number of *S. mutans* cells so determined to the amount in a sample from a normal control, i.e. a subject free from dental caries. The normal range for *S. mutans* can be determined using any of the above detection methods (i.e. detecting labeled antibody to *S. mutans*) and quantifying the amount of *S. mutans* in a normal subject or subjects free of dental caries. For example, a normal range can be 1 cell/ml to approximately $1\times10^5$ cells/ml or $1\times10^5$ cells/ml to $1\times10^6$ cell/ml. Other ranges are possible. If the subject has a measurably higher amount of *S. mutans* present that is outside of the normal range it would indicate the early onset of dental caries in the subject.

The invention also includes a method for monitoring the course of dental caries in a subject. One can test teeth or a saliva, plaque, or tartar sample from a subject with the antibodies of the invention at different points in time and determine if there has been a change in the level of *S. mutans* present. An increase over a previous reading for that individual would suggest increased caries activity. For example if a first test of a subject's saliva sample gave a result of less than $1\times10^5$ *S. mutans* cells/ml and a sample taken at a later time gave a result of greater than $1\times10^5$ *S. mutans* cells/ml it would indicate that the subject now has an increased risk of dental caries.

The invention further comprises a method of protecting teeth from dental caries by topically applying an SWLA1, SWLA2, or SWLA3 antibody, or a fragment thereof containing the *S. mutans* antigen binding activity, to teeth of a subject. The antibody can be applied topically to the surface of the teeth by means of for example, of a toothpaste, mouthwash, lozenge, gel, powder, spray, liquid, tablet, or chewing gum formulated using standard methods. The antibody can be linked to a toxic agent that kills the bacteria and applied to the surface of the teeth by, for example, any of the above methods. The proper dose of the monoclonal antibodies of the invention can be easily determined using methods which are well known to one skilled in the art (see, generally, Goodman et al. (ed.), 1993).

The methods described herein for detecting *S. mutans* may be performed using diagnostic kits (e.g., U.S. Pat. No. 5,141,850 issued Aug. 25, 1992; U.S. Pat. No. 5,202,267 issued Apr. 13, 1993; U.S. Pat. No. 5,571,726 issued Nov. 5, 1996; U.S. Pat. No. 5,602,040 issued Feb. 11, 1997). Such kits include at least one monoclonal antibody of the invention and reagents for detecting the binding of the monoclonal antibody to *S. mutans* cells present on teeth in or in a sample, e.g. of saliva, taken from a subject. The reagents include agents capable of detection, for example by fluorescence and ancillary agents such as buffering agents. The kits may also include an apparatus or container for conducting the methods of the invention and/or for transferring samples to a diagnostic laboratory for processing, as well as suitable instructions for carrying out the methods of the invention.

ADVANTAGES OF THE INVENTION

With the monoclonal antibodies of the invention it is possible to monitor the detailed topology and proportion of S. *mutans* relative to other bacterial species during the course of plaque formation and the initiation and progression of carious lesions in a subject (e.g. with fluorescence microscopy). This in turn can lead to the development of improved treatment of dental caries. For example, antibodies of the invention can be conjugated with a regular or fluorescent dye. A solution containing such antibodies can be used to rinse a patient's mouth. The dyelinked antibodies can bind to the location of the dental caries. The dental caries image can be shown on a TV screen through a video or digital micro-camera.

With the fluorescent dye-linked monoclonal antibody and video imaging techniques, it is possible to label the bacteria at infection sites and thereby assist in detecting carious lesions at an early stage and in determining whether or not the lesion is active. This aids diagnosis, treatment and improves the management of dental health.

The monoclonal antibody based detection methods of the invention allows a rapid, accurate, and economic way to quantitatively measure the *S. mutans* in a subject, with significant advantages compared to current methods. As the first step towards development of effective and accurate caries risk assessment systems, we have described methods in this study that combine monoclonal antibodies with fluorometry techniques for detection and enumeration of *S. mutans*. These methods, especially flow cytometry, are able to rapidly detect the bacterium with high specificity and enumerate it with high accuracy. With these methods, it will be possible to process a large number of saliva samples in a short period of time at low cost. This will allow low cost, accurate assays to reevaluate the correlation between the salivary count of *S. mutans* and the presence and rate of progression of dental caries. Such assays can consists of monoclonal antibodies linked to a colloidal gold calorimetric system on test strips. The invention includes the use of a test system for rapid and simple assay of *S. mutans* by color change with simple immersion in fresh saliva. Such a method is suitable for use at a dentist's chairside as well as in the patient's household to assess dental caries risk. The accurate and objective assessment of dental caries risk state and/or caries activity state with any of these or with similar technologies will permit targeted preventive and curative treatment, thereby significantly improving human dental health.

In order that the invention described herein may be more fully understood, the following example is set forth. It should be understood that this example is for illustrative purposes only and is not to be construed as limiting the scope of this invention in any manner.

EXAMPLE 1
MATERIALS AND METHODS
Bacterial Strains and Culture Conditions.

Bacterial strains used are listed in Table 2. *S mutans* was grown in Brain-Heart Infusion (BHI) medium (Difco) with supplementations of haemin (5 μg/ml). Other bacteria were grown in various media as suggested by the American Type Culture Collection (ATCC). The anaerobic bacteria were grown in an atmosphere of 80% $N_2$, 10% $CO_2$ and 10% $H_2$ at 37° C.

Production and Screening of Species-specific Monoclonal Antibodies Against *S. mutans*.

Type c *S. mutans* strain ATCC25175 were grown to log phase in BHI medium and washed twice with phosphate buffered saline pH 7.2 (PBS) by centrifuigation at 3000×g for 5 min. The pellet was resuspended in 1% formnalin/0.9% NaCl, mixed at room temperature (RT) for 30 min and washed twice with 0.9% NaCl. BALB/c mice (8–10 weeks) were immunized intraperitoneally with 100 μl of the antigen containing approximately $10^8$ whole cells of formalinized intact *S. mutans* bacteria emulsified with Freund's incomplete adjuvant (FIA). After 3–5 weeks they received a second dose of antigen ($10^8$ whole cells of bacteria in FIA). Three days prior to fusion, the mice were boosted intravenously with $10^8$ whole cells in saline.

The standard tissue culture media was RPMI 1640 (Gibco) medium supplemented with 2 mM L-glutamine, 1 mM sodium pyruvate, and 10 mM HEPES and containing 100 μg/ml penicillin and 100 μg/ml streptomycin with 10% fetal calf serum. Hybrids were selected in media containing HAT (100 μg Hypoxanthine, 0.4 PLM Aminopterin; 16 μM Thymidine). HT (100 μg Hypoxanthine, 16 μM Thymidine) was maintained in the culture medium for 2 weeks after aminopterin was withdrawn. OPI (1 mM oxaloacetate, 0.45 mM pyruvate and 0.2 U/ml bovine insulin) was added as additional growth factors to the tissue culture during cloning of hybridomas. Hybridomas were raised according to the procedure reported by Kohler & Milstein (1975). The NSI/Ag4.1 mouse myeloma cell line was used as the fusion partner and grown in spinner cultures in 5% $CO_2$ at 37° C. and maintained in log phase of growth prior to fusion.

The following approach was used for screening for species-specific monoclonal antibodies against *S. mutans*. The initial screening was performed using an ELISA assay, which selects for the culture supernatants containing antibodies that bind to *S. mutans*. Formalinized bacteria were diluted in PBS to $OD_{600}$=0.5, and added to duplicate wells (100 μl) in 96 well PVC ELISA plates preincubated for 4 h with 100 μl of 0.02 mg/ml Poly-L-lysine. These antigen-coated plates were incubated overnight at 4° C. in a moist box then washed 3 times with PBS and blocked with 0.5% fetal calf serum in PBS and stored at 4° C. A volume (100 μl) of mature hybridoma supernatants were added to the appropriate wells of the antigen plates, incubated for 1 hr at room temperature, washed 3 times with PBS-0.05% Tween 20, and bound antibody was detected by the addition of polyvalent goat-anti-mouse IgG antibody conjugated with alkaline phosphatase diluted 1:1000 with PBS-1% fetal calf serum. After the addition of the substrate, 1 mg/ml p-nitrophenyl phosphate in carbonate buffer (15 mM $Na_2CO_3$, 35 mM $NaH_2CO_3$, 10 mM $MgCl_2$ pH 9.6), the color development after 15 min was measured in an EIA reader at 405 nm. The positive supernatants (3 fold higher than control) were then subjected to the immunoprecipitation assay (mixing 100 μl bacteria with 100 μl supernatant) to screen for those with strong positive reactivity. These supernatants were then used to test crossreactivity with the following bacteria (strains listed in Table 2); *Streptococcus mutans, Streptococcus rattus, Streptococcus gordonii, Streptococcus mitis, Streptococcus sobrinus, Streptococcus sanguis, Streptococcus anginosus, Lactobacillus acidophilus, Lactobacillus casei, Actinobacillus actinomycetemcomitans, Porphyromonas gingivalis, Prevotella intermedia, Bacteroidesforsythus, Eikenella corrodens, Fusobacterium nucleatur, Treponema denticola, Campylobacter rectus, Myxococcus xanthus,* and *Escherichia coli.* The results are shown in Table 2.

Detecting *S. mutans* with Fluorescence Microscopy.

A volume (10 μl) of bacterial solution was mixed with 5 μl of culture supernatant and incubated at room temperature for 20 seconds, then 1 μl fluorescein isothiocyanate (FITC) linked goat-anti-mouse IgG antibody (Sigma) was added to the solution. The mixture was placed onto a Hausser bacterial counting chamber (Bright-line 1475) and observed with a fluorescent microscope (Zeiss Axiophot) for enumeration of the bacteria.

Detecting *S. mutans* with a Fluorometer.

The bacteria were labeled with FITC molecules in the same way described above. The mixture was washed twice with PBS by centrifugation to remove the excess FITC-linked goat-anti-mouse antibody in solution. The pellet was then resuspended in PBS solution and put into a fluorometer (TD700, Turner Designs, Sunnyvale, Calif.) to measure the FITC fluorescent dyes bound to *S. mutans*, which reflects the bacterial concentration in the sample.

Detecting *S. mutans* with Flow Cytometry.

The bacteria were labeled with FITC molecules in the same way described above and analyzed with a Fluorescence-Activated Cell Sorter (FACS) (COULTER EPICS elite flow cytometer, Coulter Corp. Miami, Fla.). The FACS machine detects every particle in a solution and separates them based on their fluorescent intensity, with a capacity of 10,000 cells per second with an accuracy of 99.99%. With FITC-linked monoclonal antibodies against *S. mutans*, the bacteria can be easily detected and enumerated by the FACS machine in any bacterial mixture.

Results

Isolation of Species-specific Monoclonal Antibodies.

Three BALB/c mice were immunized with formalinized *S. mutans* and used for production of monoclonal antibodies. The No. 2 mouse was selected because its serum showed the strongest positive reactivity with the bacterium and because 1835 mature hybridomas were obtained from this mouse.

Given the complexity of the surface of the *S. mutans* that contains a vast amount of distinct epitopes, it was important to have enough different hybridomas for binding assays in order to obtain some species-specific monoclonal antibodies. All 1835 mature hybridoma supernatants were screened with the ELISA assay, and 781 supernatants were found to have positive reactivity with *S. mutans*. Further immunoprecipitation assays identified 116 supernatants that gave the strongest positive reactivity. These culture supernatants were used to test cross-reactivity with the bacteria listed in Table 2.

TABLE 2

| Species | Strain name | Cross-reactivity | | |
|---|---|---|---|---|
| | | SWLA1 | SWLA2 | SWLA3 |
| *Streptococcus mutans* | ATCC25175 | + | + | + |
| | LM7 | + | + | + |
| | OMZ175 | + | + | + |
| | ATCC31377 | + | + | + |
| *Streptococcus rattus* | ATCC19645 | − | − | − |
| *Streptococcus gordonii* | ATCC10558 | − | − | − |
| | ATCC13396 | − | − | − |
| *Streptococcus mitis* | ATCC49456 | − | − | − |
| *Streptococcus sobrinis* | ATCC33478 | − | − | − |
| | 6715 | − | − | − |
| *Streptococcus sanguis* | ATCC10556 | − | − | − |
| | ATCC49295 | − | − | − |
| *Streptococcus anginosus* | ATCC33397 | − | − | − |
| *Lactobacillus acidophilus* | ATCC4356 | − | − | − |
| *Lactobacillus casei* | ATCC4646 | − | − | − |
| *A. actinomycetemcomitans* | ATCC33384 | − | − | − |
| *Porphyromonas gingivalis* | ATCC33277 | − | − | − |
| *Prevotella intermedia* | ATCC49046 | − | − | − |
| *Bacteroides forsythus* | ATCC43037 | − | − | − |
| *Eikenella corrodens* | ATCC23834 | − | − | − |
| *Fusobacterium nucleatum* | ATCC25586 | − | − | − |
| *Treponema denticola* | ATCC33520 | − | − | − |

TABLE 2-continued

| Species | Strain name | Cross-reactivity | | |
|---|---|---|---|---|
| | | SWLA1 | SWLA2 | SWLA3 |
| *Campylobacter rectus* | ATCC33238 | − | − | − |
| *Myxococcus xanthus* | DZ2 | − | − | − |
| *Escherichia coli* | HB101 | − | − | − |

Three supernatants were identified which had the highest positive reactivity with *S. mutans*, yet did not have any significant cross-reactivity with other bacteria listed. The three hybridomas in the supernatants were further subcloned, purified, and designated as SWLA1, SWLA2, and SWLA3. Subclass isotype analysis indicates that all three monoclonal antibodies are of IgG subclass. Western blot analysis showed that the antibodies did not cross-react with any other bacterial surface proteins, distinguishing them from the known antibodies to *S. mutans* that cross-react with proteins on the cell surface of other bacteria. These findings indicate that the antibodies of the invention most likely bind to unique polysaccharide epitope on the surface of *S. mutans*.

Enumeration of *S. mutans* with Fluorescence Microscopy.

Figure 1B:
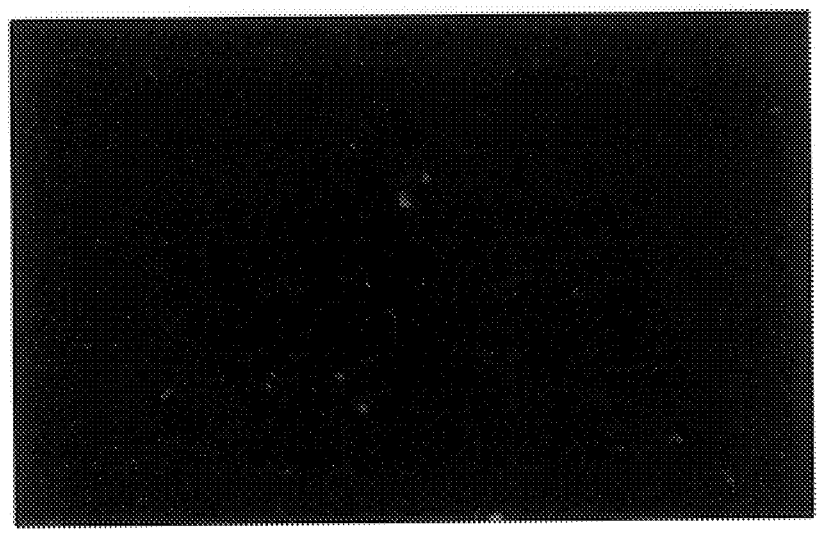
Figure 2A:
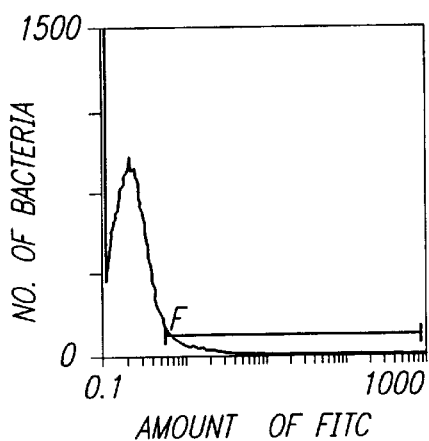
FIG. 2 shows flow cytometry analysis of S. mutans SWLAI, as described in example 1, infra; 2(a) shows S. mutans (ATCC25175) without SWLAI and FICT-linked goat-anti-mouse IgG antibody; 2(b) shows S. mutans with SWLAI and FICT-linked goat-anti-mouse IgG antibody; 2(c) shows F. nucleatum (ATCC25586) without SWLAI and FICT-linked goat-anti-mouse IgG antibody; 2(d) shows F. nucleatum with SWLAI and FICT-linked goat-anti-mouse IgG antibody; 2(e) shows T. denticola (ATCC33520) without SWLA1 and FICT-linked goat-antibody mouse IgG antibody; 2(f) shows T denticola with SWLA1 and FICT-linked goat-anti-mouse IgG antibody; F is the area containing bacterial particles labeled with FITC-linked monoclonal antibody.
Figure 2B:
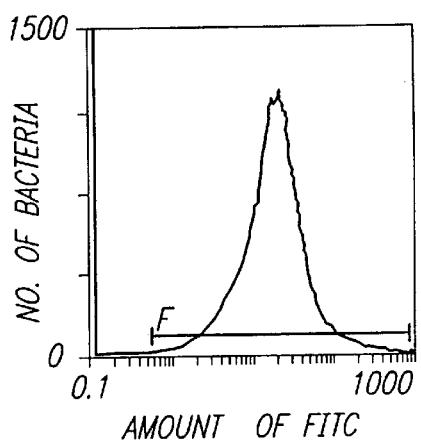
Figure 2C:
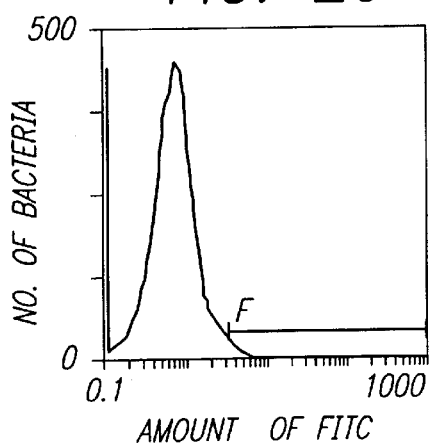
Figure 2D:
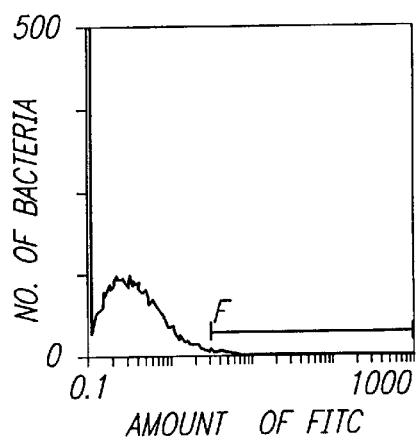
Figure 2E:
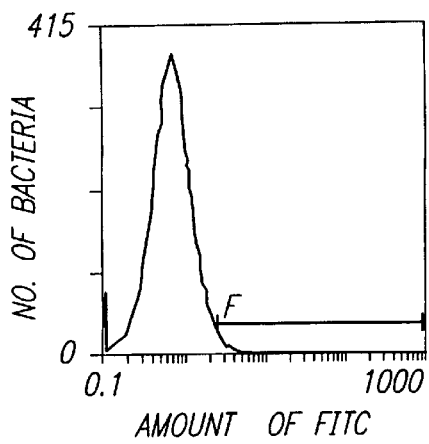
Figure 2F:
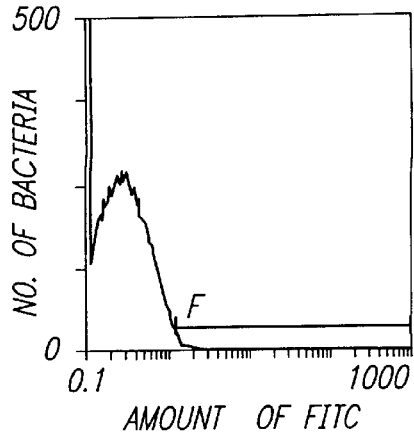

SWLA1, SWLA2 and SWLA3 antibodies were used to specifically label *S. mutans* in a mixture of bacterial cells. The monoclonal antibody-labeled *S. mutans* cells were then treated with FITC linked goat-anti-mouse IgG antibody to bind the monoclonal antibody and consequently label *S. mutans* cells with FITC. The FITC labeled *S. mutans* cells could be viewed and enumerated directly using a fluorescence microscope. FIG. 1(*a*). shows a microscopic image of a bacterial mixture containing *E rattus, S gordonii, S. mitis, S. sanguis, E. coli* as well as *S. mutans*. When the phase contrast lighting was shifted to fluorescent lighting, only *S. mutans* cells exhibited a fluorescent image due to bound FITC molecules, while other bacteria did not (FIG. 1(*b*).). In this way, the number of *S. mutans* in the mixture was easily recognized and enumerated. We compared this method of enumeration with the conventional colony counting method (the colony counting was performed by diluting bacteria with PBS and plating on BHI plates) and found good correlation between the two methods (Table 3).

TABLE 3

| No. of bacteria assayed by colony counting[1] (cells/ml) | No. of bacteria assayed by fluorescent microscopy[1] (cells/ml) |
|---|---|
| 1.  5.63 × 10$^6$ | 4.8 × 10$^6$ |
| 2.  4.72 × 10$^5$ | 5.2 × 10$^5$ |
| 3.  5.14 × 10$^4$ | 5.0 × 10$^4$ |

[1]The numbers listed are the average of triplicates.

Enumeration of *S. mutans* with Fluorometer.

As described above, *S. mutans* cells in a solution can be fluorescence-labeled with the monoclonal antibodies of the invention plus FITC-linked goat-anti-mouse IgG antibody, and the amount of fluorescence can be measured with a fluorometer. A linear correlation was observed between the amounts of fluorescence and concentrations of *S. mutans* in the solutions assayed by the conventional colony counting method (the colony counting was performed by diluting bacteria with PBS and plating on BHI plates.) (see Table 4).

TABLE 4

| No. of bacteria assayed by colony counting[2] (cells/ml) | Fluorescence intensity detected by a fluorometer[2,3] (arbitrary unit) |
|---|---|
| 1.  $1.5 \times 10^6$ | $2262 \pm 12$ |
| 2.  $1.3 \times 10^5$ | $228 \pm 1$ |
| 3.  $1.6 \times 10^4$ | $23 \pm 1$ |
| 4.  $1.4 \times 10^3$ | $3 \pm 1$ |

Automated Enumeration of S. mutans with Fluorescence-activated Cell Sorter.

The FITC labeled S. mutans cells were detected and enumerated with FACS. FIG. 2 shows that the FITC-linked monoclonal antibodies which specifically bound S. mutans were effectively detected by FACS while other oral bacteria, such as F. nucleatum or T. denticola labeled with the same antibodies, showed no fluorescence, i.e. the antibodies did not bind to the other oral bacteria and were specific to S. mutans.

Conclusion

Applicants have discovered novel antibodies that are species-specific for S. mutans bacteria. These antibodies can be used to detect the presence of S. mutans in a subject thus allowing diagnose, treatment and preventative care for dental caries. This invention includes methods for a quick and inexpensive test for the presence of S. mutans.

References

Allum et al., *Surg. Ann.*, (1986) 18:41–64.

Amon et al., "Monoclonal Antibodies For Immunotargeting Of Drugs In Cancer Therapy," *Monoclonal Antibodies And Cancer Therapy*, Reisfeld et al. (eds.), pp. 243–56 (Alan R. Liss, Inc. 1985).

Borrebaeck et al. *Proc. Nat'l. Acad. Sci.* (USA) (1988) 85:3995–99.

Bradwell et al., *Monoclonal Antibodies for Cancer Detection and Therapy*, Baldwin et al. (eds.), pp. 65–85, Academic Press (1985).

Brady, L. J. et al., "Identification of monoclonal antibody-binding domains within antigen P1 of Streptococcus mutans and cross-reactivity with related surface antigens of oral streptococci," *Infect. Immun.* 59:4425–4435 (1991).

Brown et al., *J Immunol.*, 127(2):539–46 (1981).

Brown et al., *J Biol. Chem.*, 255:4980–83 (1980).

*Cancer Diagnosis In Vitro Using Monoclonal Antibodies*, Kupchik (ed.) Marcel Dekker, Inc., New York (1988).

Carlen, A. and J. Olsson, "Monoclonal antibodies against a high-molecular-weight agglutinin block adherence to experimental pellicles on hydroxyapatite and aggregation of Streptococcus mutans," *J Dent. Res.* 74:1040–1047 (1995).

Cedars-Sinai Medical Center, *Guide to laboratory services*, Lexi-Comp Inc., Hudson, Ohio. (1995).

Chia, J. S., Lin, R. H., Lin, S. W., Chen, J. Y., Yang, C. S., "Inhibition of glucosyltransferase activities of Streptococcus mutans by a monoclonal antibody to a subsequence peptide," *Infect. Immun.* 61:4689–4695 (1993).

Ciocca et al., *Meth. Enzymol.* 121:562–79 (1986).

Clark, J. K., "On the bacterial factor in the etiology of dental caries," *Brit. J. Path.* 5:141–147 (1924).

Colcher et al., *Meth. Enzymol.*, 121:802–16 (1986).

Ellen, R. P., "Microbiological assays for dental caries and periodontal disease susceptibility," *Oral Sci. Rev.* 8:3–23 (1976).

Fink, et al. *Prog. Clin. Pathol.* 9:121–33 (1984).

Fitzgerald, R. J. and P. H. Keyes, "Demonstration of the etiologic role of streptococci in experimental caries in the hamster," *JADA* 671:9–19 (1960).

Fukushima K., Okada T., Ochiai K., "Production, characterization, and application to monoclonal antibodies which distinguish three glucosyltransferases from Streptococcus mutans," *Infect. Immun.*, 61:323–328 (1993).

Goodman and Gilman's The Pharmacological Basis of Therapeutics, 8th ed. (A. Gilmnan, T. Rall, A. Nies and P. Taylor: eds.) McGraw-Hill, Inc., 53:1272–1273 (1993).

Golub, E. S. and D. R. Green, *Immunology: A Synthesis*, Sinauer Associates, Inc. Sunderland, Mass. 164–166 (1991).

Harlow E. and D. Lane, "Antibodies, a laboratory manual," CSH Press, Cold Spring Harbor Laboratory, New York (1988).

Hasan, J. A. K., A. Huq, M. L. Tamplan, R. J. Siebeling, and R. R. Colwell, "A novel kit for rapid detection of Vibrio cholerae O1," *J Clin. Microbiol.*, 32:249–252 (1994).

Hellstrom et al., *Cancer Research*, 46:3917–23 (1986).

Hellstrom et al., "Antibodies For Drug Delivery", in *Controlled Drug, Delivery* (2nd Ed.), Robinson et al. (eds.), pp. 623–53 (Marcel Dekker, Inc. 1987).

Hume, W. R., "Need for change in standards of caries diagnosis-perspective based on the structure and behavior of the carious lesion," *J Dent. Educ.* 57:439–443 (1993).

Igarashi T., Yamamoto A., Goto N., "Direct detection of Streptococcus mutans in human dental plaque by polymerase chain reaction," *Oral Microbiology and Immunology*, 11:294–298 (1996).

Kimball (ed.), *Introduction To Immunology* (2nd Ed.), pp. 113–117, Macmillan Publ. Co (1986).

Kohler G., and C. Milstein, "Continuous cultures of fused cells secreting antibody of predefined specificity," *Nature*, 256:495–497 (1975).

Krasse, B., "The cariogenic potential of foods—a critical review of current methods," *Inter. Dent. J.* 35:36–42 (1985).

Krasse B., "Biological factors as indicators of future caries," *Inter. Dent. J.* 38:219–225 (1985).

Liu et al., *Proc. Natl. Acad Sci.* (USA) 84:3439–43 (1987).

Loesche, W. J., "Dental Caries: a treatable infection," Thomas, Springfield (1982).

Loesche, W. J., "Role of streptococcus mutans in human dental decay," *Microbiol. Rev.* 50:353–380 (1986).

Loesche, W. J., Rowan, J., Straffon, L. H., Loos, P. J., "Association of Streptococcus mutans with human dental decay," *Infect. Immun.* 11: 1252–1260 (1975).

*Monoclonal Antibodies in Cancer: Advances for Diagnosis and Treatment*, Roth (ed.), Futura Publishing, Mt. Kisco, N.Y. (1986).

Mundorff, S. A., Billings, R. J., Leverett, D. H., Featherstone, J. D., Gwinner, L. M., Shields, C. P., Proskin, H. M., Shaffer, C. L., "Saliva and dental caries risk assessment," *Ann. New York Acad Sci.* 694:302–304 (1993).

Oi et al., *Biotechnologies*, 4(3):214–221 (1986).

Sikora et al. (eds.), *Monoclonal* Antibodies, pp. 32–52, Blackwell Scientific Publications, (1984).

Shawler et al., *J Immunol.* 135:1530–35 (1985).

Tanzer, J. M., "Understanding dental caries: an infectious disease, not a lesion," *Inter. J Oral Biol.* 22:205–214 (1997).

Thorpe "Antibody Carriers Of Cytotoxic Agents In Cancer Therapy: A Review", in *Monoclonal Antibodies '84: Biological And Clinical Applications*, Pinchera et al. (eds.), pp. 475–506 (1985).

Thorpe et al., "The Preparation And Cytotoxic Properties Of Antibody-Toxin Conjugates", *Immunol. Rev.*, 62:119–58 (1982).

Uotila et al., *J Immunol. Methods*, 42:11 (1981).

Van Houte, J., "Microbiological predictors of caries risk," *Adv. Dent. Res.* 7:80–86 (1993).

Wensel and Meares, *Radio Immunoimaging and Radioimmunotherapy*, Esevier, N.Y. (1983).

Yeh et al., *Proc. Nat'l. Acad Sci.* (USA), 76 (6):2927–31 (1976).

Yeh et al., *Int. J Cancer*, 29:269–75 (1982).

Zola et al., "Monoclonal Hybridoma Antibodies: Techniques And Applications", Hurell (ed.) pp. 51–52 (CRC Press 1982).

What is claimed is:

1. A monoclonal antibody that specifically binds an antigen on the surface of *Streptococcus mutans* and which is the monoclonal antibody produced by a hybridoma deposited with the American Type Culture Collection as ATCC No. HB12559, and which is designated SWLA1.

2. A monoclonal antibody that specifically binds an antigen on the surface of *S. mutans* and which is the monoclonal antibody produced by a hybridoma deposited with the American Type Culture Collection as ATCC No. HB 12560, and which is designated SWLA2.

3. A monoclonal antibody that specifically binds an antigen on the surface of *S. mutans* and which is the monoclonal antibody produced by a hybridoma deposited with the American Type Culture Collection as ATCC No. HB 12258, and which is designated SWLA3.

4. A hybridoma deposited with the American Type Culture Collection as ATCC No. HB 12559 producing a monoclonal antibody designated SWLA 1 specifically binding an antigen produced by *Streptococcus mutans*.

5. A hybridoma deposited with the American Type Culture Collection as ATCC No. HB 12560 producing a monoclonal antibody designated SWLA 2 specifically binding an antigen produced by *Streptococcus mutans*.

6. A hybridomna deposited with the American Type Culture Collection as ATCC No. HB 12558, producing a monoclonal antibody designated SWLA 3 specifically binding an antigen produced by *Streptococcus mutans*.

* * * * *